US00PP20563P2

(12) United States Plant Patent
van Huylenbroeck

(10) Patent No.: US PP20,563 P2
(45) Date of Patent: Dec. 15, 2009

(54) *HIBISCUS* PLANT NAMED 'DVPAZURRI'

(50) Latin Name: *Hibiscus syriacus*
Varietal Denomination: DVPazzurri

(75) Inventor: Johan van Huylenbroeck, Melle (BE)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 12/287,023

(22) Filed: Oct. 1, 2008

(51) Int. Cl.
*A01H 5/00* (2006.01)

(52) U.S. Cl. ..... Plt./257

(58) Field of Classification Search ..... Plt./257
See application file for complete search history.

*Primary Examiner*—Susan B McCormick Ewoldt

(74) *Attorney, Agent, or Firm*—C. A. Whealy

(57) ABSTRACT

A new and distinct cultivar of *Hibiscus* plant named 'DVPazurri', characterized by its relatively compact, upright and somewhat outwardly spreading plant habit; vigorous growth habit; freely branching habit; large sterile blue-colored flowers; and good garden performance.

1 Drawing Sheet

Botanical designation: *Hibiscus syriacus*.
Cultivar denomination: 'DVPazurri'.

BACKGROUND OF THE INVENTION

The present invention relates to a new and distinct cultivar of *Hibiscus*, botanically known as *Hibiscus syriacus*, commercially known as Rose-of-Sharon or Althea, and hereinafter referred to by the name 'DVPazurri'.

The new *Hibiscus* plant is a product of a planned breeding program conducted by the Inventor in Melle, Belgium. The objective of the breeding program was to develop new *Hibiscus* cultivars with unique flower coloration, uniform plant habit and hardiness.

The new *Hibiscus* plant originated from a cross-pollination during the summer of 2000 of *Hibiscus syriacus* 'Oiseau Bleu', not patented, as the female, or seed, parent with an unnamed proprietary selection of *Hibiscus syriacus*, not patented, as the male, or pollen, parent. The new *Hibiscus* plant was discovered and selected by the Inventor in September, 2003 as a flowering plant within the progeny of the stated cross-pollination in a controlled outdoor nursery environment in Melle, Belgium.

Asexual reproduction of the new *Hibiscus* plant by softwood cuttings in a controlled greenhouse environment in Melle, Belgium has shown that the unique features of this new *Hibiscus* plant are stable and reproduced true to type in successive generations of asexual reproduction.

SUMMARY OF THE INVENTION

Plants of the new *Hibiscus* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'DVPazurri'. These characteristics in combination distinguish 'DVPazurri' as a new and distinct cultivar of *Hibiscus:*

1. Relatively compact, upright and somewhat outwardly spreading plant habit.
2. Vigorous growth habit.
3. Freely branching habit.
4. Large sterile blue-colored flowers.
5. Good garden performance.

Plants of the new *Hibiscus* can be compared to plants of the female parent, 'Oiseau Bleu'. Plants of the new *Hibiscus* differ primarily from plants of 'Oiseau Bleu' primarily in plant and flower size as plants of the new *Hibiscus* are more compact and have larger flowers than plants of 'Oiseau Bleu'. In addition, flowers of plants of the new *Hibiscus* are sterile whereas flowers of plants of 'Oiseau Bleu' are fertile and produce seeds.

Plants of the new *Hibiscus* can be compared to plants of the male parent selection. Plants of the new *Hibiscus* differ primarily from plants of the male parent selection in fertility as plants of the male parent are fertile and produce seeds.

Plants of the new *Hibiscus* can be compared to plants of the *Hibiscus syriacus* 'Marina', disclosed in U.S. Plant Pat. No. 12,680. In side-by-side comparisons conducted in Melle, Belgium, plants of the new *Hibiscus* differed from plants of 'Marina' primarily in plant size as plants of the new *Hibiscus* were more compact than plants of 'Marina'. In addition, flowers of plants of the new *Hibiscus* were sterile whereas flowers of plants of 'Marina' were fertile and produced seeds.

BRIEF DESCRIPTION OF THE PHOTOGRAPHS

The accompanying colored photographs illustrate the overall appearance of the new *Hibiscus*, showing the colors as true as it is reasonably possible to obtain in colored reproductions of this type. Colors in the photographs may differ slightly from the color values cited in the detailed botanical description which accurately describe the colors of the new *Hibiscus*.

The photograph at the bottom of the sheet is a side perspective view of a typical plant of 'DVPazurri' grown in an outdoor nursery.

The photograph at the top of the sheet is a close-up view of a typical opening flower of 'DVPazurri'.

DETAILED BOTANICAL DESCRIPTION

The aforementioned photographs and following observations, measurements and values describe plants grown in Grand Haven, Mich. during the summer in an outdoor nursery and under conditions which closely approximate commercial production. Plants were four years old when the photographs and the description were taken. In the description, color references are made to The Royal Horticultural Society Colour Chart, 1995 Edition, except where general terms of ordinary dictionary significance are used.

Botancial classification: *Hibiscus syriacus* 'DVPazurri'.

Parentage:

*Female, or seed, parent.*—*Hibiscus syriacus* 'Oiseau Bleu', not patented.

*Male, or pollen, parent.*—Unnamed seedling selection of *Hibiscus syriacus*, not patented.

Propagation:

*Type.*—By softwood cuttings.

*Time to initiate roots.*—About three weeks at 27° C.

*Time to produce a rooted young plant.*—About four months at 27° C.

*Root description.*—Fine to thick.

*Rooting habit.*—Freely branching; dense.

Plant description:

*Plant form and growth habit.*—Perennial shrub. Relatively compact, upright and somewhat outwardly spreading plant habit; vigorous growth habit.

*Branching habit.*—Freely branching, usually about 22 lateral branches develop per plant after pinching (removal of terminal apices).

*Plant height.*—About 100 cm.

*Plant diameter* (*area of spread*).—About 75 cm.

Lateral branch description:

*Length.*—About 40 cm.

*Diameter.*—About 4 mm.

*Internode length.*—About 4 cm to 6 cm.

*Texture, immature.*—Smooth, glabrous.

*Texture, mature.*—Woody.

*Color, immature.*—Close to 137A.

*Color, mature: Between* 191A and 198A.

Foliage description:

*Arrangement.*—Alternate, simple.

*Length.*—About 9.5 cm.

*Width.*—About 5.5 cm.

*Shape.*—Ovate to rhomboid.

*Apex.*—Acute.

*Base.*—Cuneate.

*Margin.*—Crenate; lobed.

*Texture, upper and lower surfaces.*—Smooth, glabrous.

*Venation pattern.*—Palmate.

*Color.*—Developing and fully expanded leaves, upper surface: Close to 146A; venation, close to 146B. Developing and fully expanded leaves, lower surface: Close to 146B; venation, close to 146B.

*Petiole.*—Length: About 1 cm. Diameter: About 2 mm. Texture, upper and lower surfaces: Smooth, glabrous. Color, upper and lower surfaces: Close to 146A.

Flower description:

*Flower appearance/arrangement.*—Single rotate flowers; terminal and axillary. Freely flowering habit with usually about 5 to 13 flowers per lateral branch. Flowers face upright to outwardly.

*Flower longevity.*—Flowers last for about one to two days on the plant; flowers not persistent.

*Natural flowering season.*—Typically during the months of July and August in Mich.

*Fragrance.*—None detected.

*Flower diameter.*—About 11 cm.

*Flower length* (*height*).—About 6 cm.

*Flower bud.*—Length: About 1.8 cm. Diameter: About 1.8 cm. Shape: Ovate. Color: Close to 146C.

*Petals.*—Arrangement/quantity: Single whorl of five petals; petals imbricate. Length: About 6 cm. Width: About 6 cm. Shape: Ovate. Apex: Broadly obtuse, rounded. Base: Attenuate. Margin: Entire; undulate. Texture, upper and lower surfaces: Smooth, glabrous. Color: When opening, upper surface: Center and towards the apex, close to 95B; towards the base, close to 59A. When opening, lower surface: Center and towards the apex, close to 95A; towards the base, close to 59A. Fully opened, upper and lower surfaces: Center and towards the apex, close to 97A to 97B; towards the base, close to 59A; venation, similar to petal surface color. Color becoming closer to between 96A and 97B with subsequent development.

*Sepals.*—Appearance: Five sepals fused into a campanulate-shaped calyx. Length: About 1.3 cm. Width: About 1 cm. Shape: Roughly ovate. Apex: Acute. Margin: Entire. Texture, upper and lower surfaces: Smooth, glabrous. Color, immature and mature, upper and lower surfaces: Close to 146B.

*Peduncles.*—Length: About 2.5 cm. Diameter: About 3 mm. Strength: Strong, flexible. Texture: Smooth, glabrous. Angle: About 35° to 45° from the stem. Color: Close to 146B.

*Reproductive organs.*—Androecium: Anther shape: Globular. Anther size: About 1 mm by 1 mm. Anther color: Close to 160C. Amount of pollen: Abundant. Pollen color: Close to 160C. Gynoecium: Pistil length: About 4 mm. Style length: About 3.9 cm. Style color: Close to 155A. Stigma appearance: Five-parted, globular. Stigma color: Close to 160C. Ovary color: Close to 155A.

*Seeds/fruits.*—Seed and fruit development have not been observed on plants of the new *Hibiscus* plant.

Garden performance: Plants of the new *Hibiscus* have been observed to have good garden performance and to tolerate rain, wind and temperatures ranging from about −27C. to about 37° C.

Pathogen/pest resistance: Plants of the new *Hibiscus* have not been shown to be resistant to pathogens and pests common to *Hibiscus*.

It is claimed:

1. A new and distinct *Hibiscus* plant named 'DVPazurri' as illustrated and described.

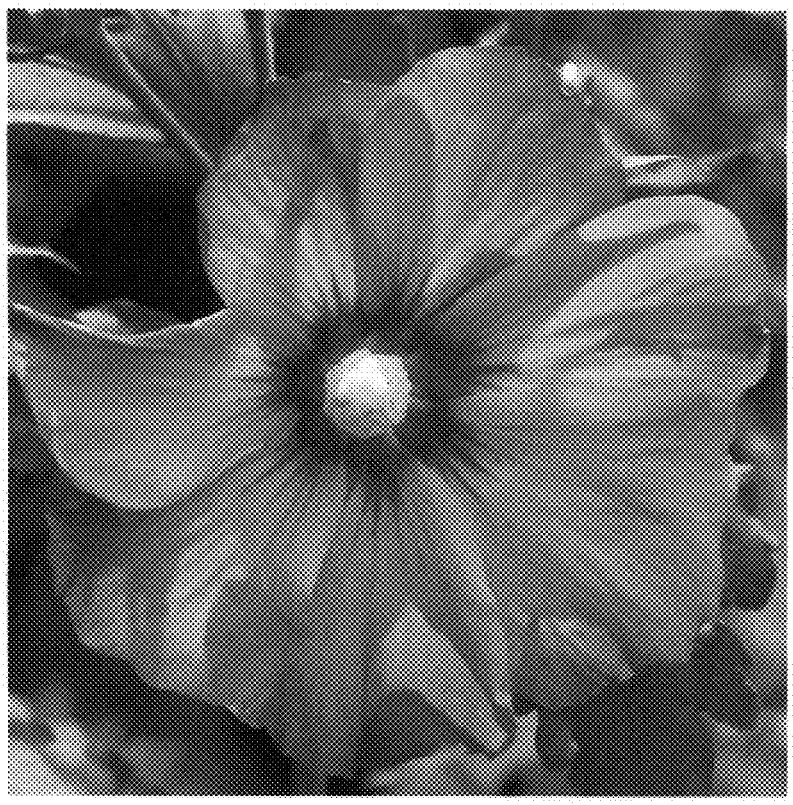
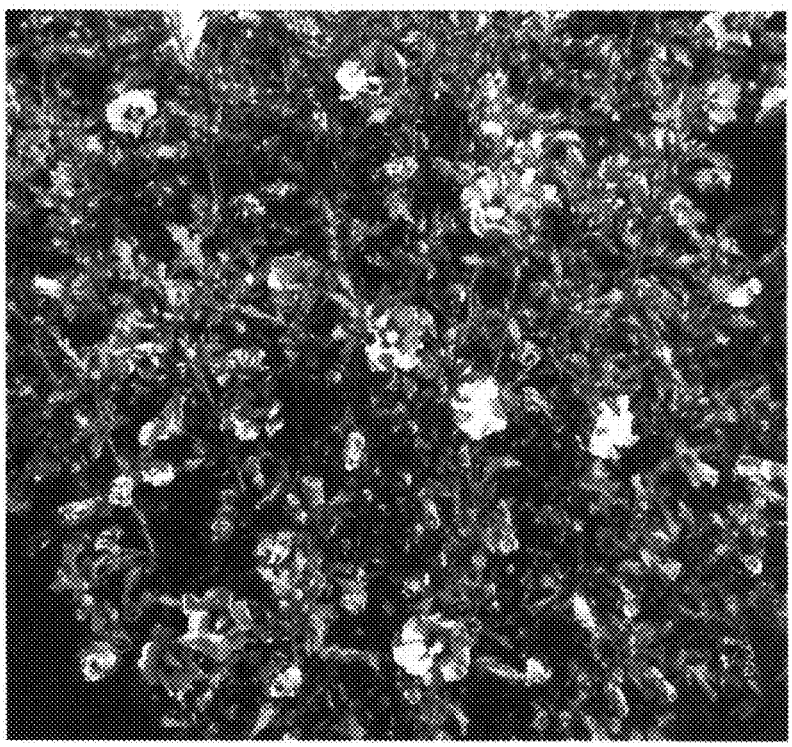

* * * * *